US010350203B2

(12) United States Patent
Blaise

(10) Patent No.: US 10,350,203 B2
(45) Date of Patent: *Jul. 16, 2019

(54) MULTIDRUG INFUSION FOR PAIN CONTROL

(71) Applicant: Gilbert Blaise, Montreal (CA)

(72) Inventor: Gilbert Blaise, Montreal (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/157,716

(22) Filed: May 18, 2016

(65) Prior Publication Data

US 2016/0263105 A1 Sep. 15, 2016

Related U.S. Application Data

(63) Continuation-in-part of application No. 14/845,546, filed on Sep. 4, 2015, now abandoned.

(60) Provisional application No. 62/045,750, filed on Sep. 4, 2014.

(51) Int. Cl.
| | | |
|---|---|---|
| *A61K 31/135* | (2006.01) | |
| *A61K 31/4168* | (2006.01) | |
| *A61K 31/485* | (2006.01) | |
| *A61K 31/445* | (2006.01) | |
| *A61K 45/06* | (2006.01) | |
| *A61K 9/00* | (2006.01) | |

(52) U.S. Cl.
CPC .......... *A61K 31/485* (2013.01); *A61K 31/135* (2013.01); *A61K 31/4168* (2013.01); *A61K 31/445* (2013.01); *A61K 45/06* (2013.01); *A61K 9/0019* (2013.01); *A61K 9/0085* (2013.01)

(58) Field of Classification Search
CPC .............. A61K 31/135; A61K 31/4168; A61K 31/445; A61K 31/485; A61K 2300/00; A61K 45/06
See application file for complete search history.

(56) References Cited

U.S. PATENT DOCUMENTS

| | | | | |
|---|---|---|---|---|
| 2007/0021801 | A1* | 1/2007 | Heruth | A61M 5/14276 607/46 |
| 2007/0043120 | A1* | 2/2007 | Beyreuther | A61K 31/165 514/616 |
| 2016/0067175 | A1 | 3/2016 | Blaise | |

FOREIGN PATENT DOCUMENTS

CA 2903758 A1 3/2016

OTHER PUBLICATIONS

Blaise et al 'Continuous Intrathecal Analgesia for Severe Metastic Cancer Pain' Canadian Journal of Anesthesia, vol. 58, Supplement 1, p. S147, 2011.*
Blaise (Canadian Journal of Anesthesia vol. 58 SUPPL p. S147 Published 2011) (Year: 2011).*
Gentili (British Journal of Anesthesiology vol. 76 pp. 872-873. Published 1996). (Year: 1996).*
Eisenach et al (Anesthesiology vol. 83 pp. 1036-1045 published 1995) (Year: 1995).*
Vranken et al., Acta Anaesthesiol. Scand vol. 48, 249-252. Published 2004. (Year: 2004).*
Blaise et al., Canadian Journal of Anesthesia vol. 58 SUPPL p. S147 Published 2011. (Year: 2011).*
Gentili et al., British Journal of Anesthesiology vol. 76 pp. 872-873. Published 1996. (Year: 1996).*
Vranken et al (Anaesthesiologica Scandinavica vol. 48 pp. 249-252 published 2004) (Year: 2004).*
Blaise (Anesthesie, 2011 Annual Meeting of the Canadian Anesthesiologists Society, Presented Jun. 24, 2011) (Year: 2011).*
Anonymous "Abstract"; Canadian Journal of Anaesthesia / Journal canadien d'Anesthesie; vol. 58, No. S1; Jun. 2011; pp. S1-S170.
Chia et al. "Adding Ketamine in a Multimodal Patient-Controlled Epidural Regimen Reduces Postoperative Pain and Analgesic Consumption"; Anesthesia & Analgesia; vol. 86; Jun. 1998; pp. 1245-1249.
Blaise "Should we Use Naloxone Epidurally"; Canadian Journal of Anaesthesia ; vol. 50, No. 9; Nov. 2003; pp. 875-878.
Rosenberg et al. "Introduction"; Techniques in Regional Anesthesia and Pain Manage; W.B. Saunders, Amsterdam, NL; vol. 2, No. 2, Apr. 1998; pp. 67-68.
Knight et al. "Implantable Intrathecal Pumps for Chronic Pain: Highlights and Updates"; Croatian Medical Journal; Feb. 2007; pp. 22-34.
European Search report of corresponding European Application No. 16177609.1; Silke Albrecht; dated Sep. 13, 2017; Munich.
Committee on Advancing Pain Research, Care, and Education, Institute of Medicine. Relieving pain in America: A blueprint for transforming prevention, care, education, and research [online]. Retrieved from the Internet: <URL: http://www.iom.edu/~/media/Files/Report%20Files/2011/Relieving-Pain-in-America-A-Blueprint-for-Transforming-Prevention-Care-Education-Research/Pain%20 Research%202011 %20Report %20Brief.pdf.
Deandrea et al. "Prevalence of undertreatment in cancer pain. A review of published literature", Annals of Oncology, 2008, vol. 19, pp. 1985-1991.
Costantini et al. "Prevalence, distress, management, and relief of pain during the last 3 months of cancer patients' life. Results of an Italian mortality follow-back survey", Annals of Oncology, 2009, vol. 20, pp. 729-735.

(Continued)

*Primary Examiner* — Timothy P Thomas
*Assistant Examiner* — George W Kosturko
(74) *Attorney, Agent, or Firm* — Benoit & Cote Inc.; France Cote

(57) ABSTRACT

The present invention relates to a formulation comprising an opioid, a Na channel blocker, an alpha2-receptor agonist, an opioid mu or delta receptor competitive antagonist and an intravenous anesthetic and/or a neurologic acting agent for use in pain control and/or cognitive function improvement.

4 Claims, 1 Drawing Sheet

(56) References Cited

OTHER PUBLICATIONS

Breivik et al. "Cancer-related pain: a pan-European survey of prevalence, treatment, and patient attitudes", Annals of Oncology, 2009, vol. 20, pp. 1420-1433.
Apolone et al. "Cancer Pain Outcome Research Study Group (CPOR SG) Investigators. Pattern and quality of care of cancer pain management. Results from the Cancer Pain Outcome Research Study Group", British Journal of Cancer, 2009, vol. 100, pp. 1566-1574.
Hong et al. "Change in cancer pain management in Korea between 2001 and 2006: results of two nationwide surveys", Journal of Pain Symptom Management, Jan. 2011, vol. 41, No. 1, pp. 93-103.
Atkinson et al. "Medication Pain Management in the Elderly: Unique and Underutilized Analgesic Treatment Options", Clinical Therapeutics, Nov. 2013, vol. 35, No. 11, pp. 1669-1689.
Vissers et al. "Pain in patients with cancer", Pain Practice, 2011, vol. 11, No. 5, pp. 453-475.
Cohen et al. "Intrathecal analgesia", Anesthesiology Clinics, 2007, vol. 25, pp. 863-882.
Ver Donck et al. "Intrathecal Drug Administration in Chronic Pain Syndromes", Pain Practices, 2014, vol. 14, No. 5, pp. 461-476.
Van Dongen et al. "Long-tens intrathecal infusion of morphine and morphine/bupivacaine mixtures in the treatment of cancer pain: a retrospective analysis of 51 cases", Pain 1993, vol. 55, pp. 119-123.
Ghafoor et al. "Intrathecal drug therapy for long-term pain management", Am J Health Syst Pharm, Dec. 2007, vol. 64, pp. 2447-2461.
Aguado et al. "Effects of Naloxone on Opioid-induced Hyperalgesia and Tolerance to Remifentanil under Sevoflurane Anesthesia in Rats", Anesthesiology, May 2013, vol. 118, No. 5, pp. 1160-11699.
Taylor et al. "Opioid antagonists for pain", Expert Opinion on Investigational Drugs, 2013, vol. 22, No. 4, pp. 517-525.
Mattioli et al. "Ultra-low dose naltrexone attenuates chronic morphine-induced gliosis in rats", Molecular Pain, 2010, vol. 6, No. 22.
Lunzer et al. "Naloxone acts as a potent analgesic in transgenic mouse models of sickle cell anemia", PNAS, Apr. 3, 2007, vol. 104, No. 14, pp. 6061-6065.
Yang et al. "Ultra-Low Dose Naloxone Enhances the Antihyperalgesic Effects of Morphine and Attenuates Tumor Necrosis Factor-α and Tumor Necrosis Factor-α Receptor 1 Expression in the Dorsal Horn of Rats with Partial Sciatic Nerve Transection", Anesthesia Analgesia, Dec. 2013, vol. 117, No. 6, pp. 1493-1502.
Hamann et al. "Low-dose intrathecal naloxone to enhance intrathecal morphine analgesia: a case report", Journal of Opioid Management, Jul./Aug. 2008, vol. 4, No. 4, pp. 251-254.
Tsai et al. "Ultra-Low-Dose Naloxone Restores the Antinociceptive Effect of Morphine and Suppresses Spinal Neuroinflammation in PTX-Treated Rats", Neuropsychopharmacology, 2008, vol. 33, pp. 2772-2782.
Hsu et al. "Nanomolar Naloxone Attenuates Neurotoxicity Induced by Oxidative Stress and Survival Motor Neuron Protein Deficiency", Neurotox Res, 2014, vol. 25, pp. 262-270.
Fisher et al. "Targeting the N-Methyl-D-Aspartate Receptor for Chronic Pain Management. Preclinical Animal Studies, Recent Clinical Experience and Future Research Directions", Journal of Pain and Symptom Management, Nov. 2000, vol. 20, No. 5, pp. 358-373.
Mei et al. "Ketamine Depresses Toll-Like Receptor 3 Signaling in Spinal Microglia in a Rat Model of Neuropathic Pain", Neurosignals, 2011, vol. 19, pp. 44-53.
Mion et al. "Compassionate use of intrathecal ketamine for intractable cancer pain (Lett)", Ann Fr Anesth Reanim, 2013, vol. 32, pp. 621-622.
Rojas et al. "The Effects of Subarachnoid Administration of Preservative-Free S(+)-Ketamine on Spinal Cord and Meninges in Dogs", Anesthesia Analgesia, Feb. 2012, vol. 114, No. 2, pp. 450-455.
Karpinski et al. "Subpial vacuolar myelopathy after intrathecal ketamine: report of a case", Pain, 1997, vol. 73, pp. 103-105.
Stotz et al. "Histological Findings After Long-Term Infusion of Intrathecal Ketamine for Chronic Pain: A Case Report", Journal of Pain Symptom Management, Sep. 1999, vol. 18, No. 3, pp. 223-228.
De Kock et al. "Ketamine and Peripheral Inflammation" CNS Neuroscience Therapeutics, 2013, vol. 19, pp. 403-410.
Yan et al. "Dual Effects of Ketamine: Neurotoxicity Versus Neuroprotection in Anesthesia for the Developing Brain", J Neurosurg Anesthesiol, Apr. 2014, vol. 26, No. 2, pp. 155-160.
Sylvester et al. "The conversion challenge: from intrathecal to oral morphine", American Journal of Hospice & Palliative Medicine, Mar./Apr. 2004, vol. 21, No. 2, pp. 143-147.
Krames "Intraspinal Opioid Therapy for Chronic Nonmalignant Pain: Current Practice and Clinical Guidelines", Journal of Pain Symptom Management, Jun. 1996, vol. 11, No. 6, pp. 333-352.

\* cited by examiner

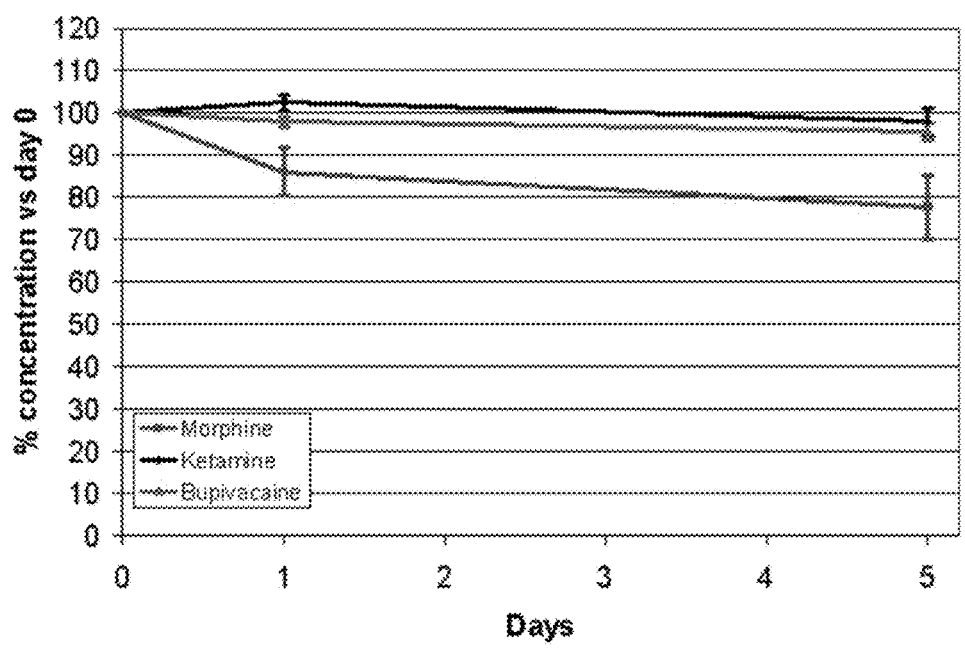

MULTIDRUG INFUSION FOR PAIN CONTROL

CROSS-REFERENCE TO RELATED APPLICATIONS

This application is a continuation-in-part application under 37 CFR 1.53(b) of U.S. patent application Ser. No. 14/845,546, filed Sep. 4, 2015, which claims priority from and the benefit of under 35 USC 119(e), of U.S. provisional patent applications U.S. 62/045,750, filed Sep. 4, 2014, the specifications of which are hereby incorporated by reference, in their entireties.

BACKGROUND

Field

Achieving effective, durable, and safe pain relief, especially in aged patients and end-stage malignancies can be a clinical challenge. Despite multimodal systemic approaches with the least doses of drugs to decrease systemic side effects, the pain is often poorly controlled with unacceptable side effects in some patients.

SUMMARY

In accordance with one embodiment of the present invention, there is provided formulation for pain control and/or cognitive functions improvement comprising:
  an opioid;
  a Na channel blocker;
  an alpha2-receptor agonist;
  an opioid mu or delta receptor competitive antagonist; and
  an intravenous anesthetic and/or a neurologic acting agent.

The administration may be intrathecally, epidurally, paraverthebrally, at the peripheral nerves level, at the nerve plexus level, intra-articularly, in a synovial bursa, sub-cutaneously, and intravenously, or combination thereof.

The opioid may be chosen from morphine, fentanyl, sufentanil, hydromorphone, tramadol, pentazocine, dianorphine, methadone, meperidine, and butorphanol.

The Na channel blocker may be chosen from bupivacaine, ropivacaine and lidocaine and any other Na channel blockers.

The alpha2-receptor agonist may be chosen from clonidine, dexmedetomidine, fadolmidine and tinazidine.

The opioid mu receptor competitive antagonist may be chosen from naloxone, naltrexone and naltrindole.

The intravenous anesthetic and/or a neurologic acting agent may be chosen from ketamine, propofol, tricyclic antidepressants such as amitryptilline, and other tricyclic medications, other antidepressants such as SSRI, and SNRI; gabapentine, pregabalin, Midazolam, Baclofen, and adenosine; other compounds acting on adenosine receptors (A1, A2, A3), neostigmine, magnesium, atropine, dexamethasone, ketorolac and other NSAID, octreotide, ziconitide, droperidol, and haloperidol.

In accordance with another embodiment of the present invention, there is provided a method of pain control and/or cognitive functions improvements in a patient which comprises administration to said patient of an infusion of the formulation of any one of claim 1, at a rate of 0.5 to 5 ml/h, continuously or intermittently.

The administration may be intrathecal, epidural, paraverthebral, at the peripheral nerves level, at the nerve plexus level, intra-articular, in a synovial bursa, sub-cutaneous, and intravenous, or combination thereof.

In accordance with another embodiment of the present invention, there is provided a kit to control pain and/or improve and/or cognitive functions in a patient which comprises:
  a catheter optionally connected to a PORT-A-CATH™; and a reservoir placed under the skin. The medication is injected in the reservoir either as a bolus or a continuous infusion through an external perfusion device is done.
  a reservoir connected to an implanted pump for receiving a formulation of the present invention and wherein the reservoir is to be connected to the catheter (no external infusion system).

The catheter may be connected to an injection means comprising pump means, reservoir and controller means to administer the formulation.

In accordance with another embodiment of the present invention, there is provided a formulation for pain control and/or cognitive functions improvement comprising:
  an opioid;
  a Na channel blocker;
  an alpha2-receptor agonist;
  an opioid mu or delta receptor competitive antagonist; and
  an intravenous anesthetic and/or a neurologic acting agent for administration epidurally, paraverthebrally, at the peripheral nerves level, at the nerve plexus level, intra-articularly, in a synovial bursa, sub-cutaneously, and intravenously, or combination thereof.

The formulation may be for epidural administration.
The formulation may be for paravertebral administration.
The formulation may be for peripheral nerve administration.
The formulation may be for nerve plexus administration.
The formulation may be for intra-articular administration.
The formulation may be for synovial bursa administration.
The formulation may be for sub-cutaneous administration.
The formulation may be for intravenous administration.

The opioid may be chosen from morphine, fentanyl, sufentanil, hydromorphone, tramadol, pentazocine, dianorphine, methadone, meperidine, and butorphanol.

The Na channel blocker may be chosen from bupivacaine, ropivacaine and lidocaine.

The alpha2-receptor agonist may be chosen from clonidine, dexmedetomidine, fadolmidine and tinazidine.

The opioid mu receptor competitive antagonist may be chosen from naloxone, naltrexone and naltrindole.

The intravenous anesthetic and/or a neurologic acting agent may be chosen from ketamine, propofol, tricyclic antidepressants such as amitryptilline, and other tricyclic medications, other antidepressants such as SSRI, and SNRI; gabapentine, pregabalin, Midazolam, Baclofen, and adenosine; other compounds acting on adenosine receptors (A1, A2, A3), neostigmine, magnesium, atropine, dexamethasone, ketorolac and other NSAID, octreotide, ziconitide, droperidol, and haloperidol.

In accordance with another embodiment of the present invention, there is provided a use of a formulation comprising:
  an opioid;
  a Na channel blocker;
  an alpha2-receptor agonist;
  an opioid mu or delta receptor competitive antagonist; and an intravenous anesthetic and/or a neurologic acting agent, for pain control and/or cognitive function improvement,
wherein said use is epidural, paravertebral, at the peripheral nerves level, at the nerve plexus level, intra-articular, in a synovial bursa, sub-cutaneous, and intravenous, or combination thereof.

In accordance with another embodiment of the present invention, there is provided a use of a formulation comprising:
an opioid;
a Na channel blocker;
an alpha2-receptor agonist;
an opioid mu or delta receptor competitive antagonist; and
an intravenous anesthetic and/or a neurologic acting agent, for the preparation of a medicament for use in pain control and/or cognitive function improvement,
wherein said medicament is for intrathecal use, epidural use, paravertebral use, use at the peripheral nerves level, use at the nerve plexus level, intra-articular use, use in a synovial bursa, sub-cutaneous use, and intravenous use, or combination thereof.

The use may be for epidural administration.
The use may be for paravertebral administration.
The use may be for peripheral nerve administration.
The use may be for nerve plexus administration.
The use may be for intra-articular administration.
The use may be for synovial bursa administration.
The use may be for sub-cutaneous administration.
The use may be for intravenous administration.

The opioid may be chosen from morphine, fentanyl, sufentanil, hydromorphone, tramadol, pentazocine, dianorphine, methadone, meperidine, and butorphanol.

The Na channel blocker may be chosen from bupivacaine, ropivacaine and lidocaine.

The alpha2-receptor agonist may be chosen from clonidine, dexmedetomidine, fadolmidine and tinazidine.

The opioid mu receptor competitive antagonist may be chosen from naloxone, naltrexone and naltrindole.

The intravenous anesthetic and/or a neurologic acting agent may be chosen from ketamine, propofol, tricyclic antidepressants such as amitryptilline, and other tricyclic medications, other antidepressants such as SSRI, and SNRI; gabapentine, pregabalin, Midazolam, Baclofen, and adenosine; other compounds acting on adenosine receptors (A1, A2, A3), neostigmine, magnesium, atropine, dexamethasone, ketorolac and other NSAID, octreotide, ziconitide, droperidol, and haloperidol.

The following terms are defined below:

The term «composition» as used herein is intended to encompass a product comprising the specified ingredients in the specified amounts, as well as any product which results, directly or indirectly, from combination of the specified ingredients in the specified amounts. Such term in relation to pharmaceutical composition or other compositions in general, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions or other compositions in general of the present invention encompass any composition made by admixing a compound of the present invention and a pharmaceutically acceptable carrier. By "pharmaceutically acceptable" or "acceptable" it is meant the carrier, diluent or excipient must be compatible with the other ingredients of the formulation and not deleterious to the recipient thereof.

The term "intravenous anesthetic and/or a neurologic acting agent" is intended to mean a drug, compound or active ingredient having a neurological effect on the subject in need thereof. For example, according to an embodiment, the neurological agent may treat, diminish, or alleviate the symptoms of a given neurological disorder. Examples of symptoms of neurological disorder include paralysis, muscle weakness, poor coordination, loss of sensation, seizures, confusion, pain and altered levels of consciousness, depression psychosis.

BRIEF DESCRIPTION OF THE DRAWINGS

Further features and advantages of the present disclosure will become apparent from the following detailed description, taken in combination with the appended drawings, in which:

FIG. 1 illustrates the stability of the drugs in the prepared solution at room temperature during five days measured by tandem mass spectrometry. Solution contains bupivacaine 1 mg/ml, ketamine 100 µg/ml, morphine 0.01 mg/ml in NaCl 0.9% 50 ml plastic bag. The concentration of ketamine and bupivacaine is stable but morphine's concentration decreases 15% on first day and then stays mostly unchanged during the following days.

DETAILED DESCRIPTION

In a first embodiment, there is disclosed a formulation for pain control and/or cognitive functions improvement comprising:
an opioid;
a Na channel blocker;
an alpha2-receptor agonist;
an opioid mu or delta receptor competitive antagonist; and
an intravenous anesthetic and/or a neurologic acting agent.

According to embodiments, the administration may be intrathecal, epidural, paravertebral, at the peripheral nerves level, at the nerve plexus level, intra-articular, in a synovial bursa, sub-cutaneous, and intravenous, or combination thereof.

The route of administration of the formulations of the present invention may include intrathecal administration, which involves an injection into the subarachnoid space so that the formulation is injected in the cerebrospinal fluid (CSF). It is useful in spinal anaesthesia, chemotherapy, or pain management applications, such as for the present invention. The formulation given this way to bypass the blood brain barrier, and that the same drug given through other means of administration would not be able to pass easily in and out into the brain and have the desired pain management and cognitive functions improvement effects.

Unexpectedly, it has now been observed that administration of the formulation of the present invention through the epidural route, the paravertebral route, at the peripheral nerves level, at the nerve plexus level, the intra-articular route, in a synovial bursa, sub-cutaneously, and intravenously were able to provide significant and efficient pain management and cognitive functions improvement.

According to another embodiment, there is disclosed a formulation for epidural administration for pain control and/or cognitive function improvement, comprising:

an opioid;
a Na channel blocker;
an alpha2-receptor agonist;
an opioid mu or delta receptor competitive antagonist; and
an intravenous anesthetic and/or a neurologic acting agent.

According to another embodiment, there is disclosed a formulation for paravertebral administration for pain control and/or cognitive function improvement, comprising:
an opioid;
a Na channel blocker;
an alpha2-receptor agonist;
an opioid mu or delta receptor competitive antagonist; and
an intravenous anesthetic and/or a neurologic acting agent.

According to another embodiment, there is disclosed a formulation for peripheral nerve administration for pain control and/or cognitive function improvement, comprising:
an opioid;
a Na channel blocker;
an alpha2-receptor agonist;
an opioid mu or delta receptor competitive antagonist; and
an intravenous anesthetic and/or a neurologic acting agent.

According to another embodiment, there is disclosed a formulation for nerve plexus administration for pain control and/or cognitive function improvement, comprising:
an opioid;
a Na channel blocker;
an alpha2-receptor agonist;
an opioid mu or delta receptor competitive antagonist; and
an intravenous anesthetic and/or a neurologic acting agent.

According to another embodiment, there is disclosed a formulation for intra-articular administration for pain control and/or cognitive function improvement, comprising:
an opioid;
a Na channel blocker;
an alpha2-receptor agonist;
an opioid mu or delta receptor competitive antagonist; and
an intravenous anesthetic and/or a neurologic acting agent.

According to another embodiment, there is disclosed a formulation for synovial bursa administration for pain control and/or cognitive function improvement, comprising:
an opioid;
a Na channel blocker;
an alpha2-receptor agonist;
an opioid mu or delta receptor competitive antagonist; and
an intravenous anesthetic and/or a neurologic acting agent.

According to another embodiment, there is disclosed a formulation for sub-cutaneous administration for pain control and/or cognitive function improvement, comprising:
an opioid;
a Na channel blocker;
an alpha2-receptor agonist;
an opioid mu or delta receptor competitive antagonist; and
an intravenous anesthetic and/or a neurologic acting agent.

According to another embodiment, there is disclosed a formulation for intravenous administration for pain control and/or cognitive function improvement, comprising:
an opioid;
a Na channel blocker;
an alpha2-receptor agonist;
an opioid mu or delta receptor competitive antagonist; and
an intravenous anesthetic and/or a neurologic acting agent.

In embodiments, the opioid may be chosen from morphine, fentanyl, sufentanil, hydromorphone, tramadol, pentazocine, dianorphine, methadone, meperidine, and butorphanol.

In embodiments, Na channel blocker may be chosen from bupivacaine, ropivacaine and lidocaine.

In embodiments, alpha2-receptor agonist may be chosen from clonidine, dexmedetomidine, fadolmidine and tinazidine.

In embodiments, the opioid mu receptor competitive antagonist may be chosen from naloxone, naltrexone and naltrindole.

In embodiments, the intravenous anesthetic and/or a neurologic acting agent may be chosen from ketamine, propofol, tricyclic antidepressants such as amitryptilline, and other tricyclic medications, other antidepressants such as SSRI, and SNRI; gabapentine, pregabalin, Midazolam, Baclofen, and adenosine; other compounds acting on adenosine receptors (A1, A2, A3), neostigmine, magnesium, atropine, dexamethasone, ketorolac and other NSAID, octreotide, ziconitide, droperidol, and haloperidol According to another embodiment, there is disclosed a method of pain control and/or cognitive functions improvements in a patient which comprises administration to said patient of an infusion of the formulation of the present invention at a rate of 0.5 to 5 ml/h, continuously or intermittently.

According to embodiments, the administration may be intrathecal, epidural, paravertebral, at the peripheral nerves level, at the nerve plexus level, intra-articular, in a synovial bursa, sub-cutaneous, and intravenous, or combination thereof.

According to another embodiment, there is disclosed the use of a formulation comprising:
an opioid;
a Na channel blocker;
an alpha2-receptor agonist;
an opioid mu or delta receptor competitive antagonist; and
an intravenous anesthetic and/or a neurologic acting agent,
for pain control and/or cognitive function improvement,
wherein said use is intrathecal, epidural, paravertebral, at the peripheral nerves level, at the nerve plexus level, intra-articular, in a synovial bursa, sub-cutaneous, and intravenous, or combination thereof.

According to another embodiment, there is disclosed the use of a formulation comprising:
an opioid;
a Na channel blocker;
an alpha2-receptor agonist;
an opioid mu or delta receptor competitive antagonist; and
an intravenous anesthetic and/or a neurologic acting agent,
for the preparation of a medicament for use in pain control and/or cognitive function improvement,
wherein said medicament is for intrathecal use, epidural use, paravertebral use, use at the peripheral nerves level, use at the nerve plexus level, intra-articular use, use in a synovial bursa, sub-cutaneous use, and intravenous use, or combination thereof.

According to another embodiment, there is disclosed a kit to control pain and/or improve and/or cognitive functions in a patient which comprises:
a catheter optionally connected to a PORT-A-CATH™; and a reservoir placed under the skin. The medication is injected in the reservoir either as a bolus or a continuous infusion through an external perfusion device is done.

a reservoir connected to an implanted pump for receiving a formulation of the present invention and wherein the reservoir is to be connected to the catheter (no external infusion system).

The present invention presents an alternative method for managing refractory pain in any type of patients. It is specially indicated for elderly and cancer-related intractable pain while improving cognitive function, based on time-limited intrathecal (IT) infusion of a multi-drug analgesic mixture. Three old patients suffering from a poorly-controlled pain were treated. A mixture of bupivacaine 1 mg/ml, naloxone 0.02 ng/ml, ketamine 100 μg/ml, morphine 0.01 mg/ml and clonidine 0.75 μg/ml was infused via IT by an external pump. The pain was successfully controlled and cognitive functions greatly improved. Oral and parenteral opioids consumption reduced dramatically. Such an IT approach could be considered as an alternative modality for intractable pain relief in elderly or in malignancies.

EXAMPLE 1

Pain Management Through Intrathecal Infusion

To explore the efficacy of an alternative method to manage pain based on time-limited intrathecal (IT) infusion of an analgesic medication mixture, three patients with the ages of 69, 64 and 94 suffering from intractable and poorly-controlled pain due to bed sores, pelvic metastatic mass and thoracic vertebra and ribs fractures, respectively, were treated. Daily dose of opioids could not be increased due to side effects. An intrathecal catheter 20G was placed by percutaneous approach in lumbar area while advancing toward thoracic region tunneled and fixed subcutaneously. It was connected to an external infusion pump with a mixture of bupivacaine 1 mg/ml, naloxone 0.02 ng/ml, ketamine 100 μg/ml, morphine 0.01 mg/ml and clonidine 0.75 μg/ml. Starting rate was 1 ml/h. The pain was mostly controlled with a rate of less than 1 ml/h. Opioid consumption was reduced dramatically. Catheter was kept for one month in first and third patient and for 6 months in the second one until his death. No major side effects such as hypotension, constipation, muscle weakness, sphincter dysfunction and cognitive or mood deterioration were observed with this approach. One patient had urinary tract infection followed by sepsis and meningitis which was easily cured by antibiotics. Catheter was removed in this patient. Intrathecal infusion with a low-concentration multi-drugs mixture could be considered as an alternative modality for intractable pain relief in elderly or malignancies. The cognitive functions of all patients were also greatly improved.

Three patients admitted in hospital became candidates of IT infusion (Table-1).

TABLE 1

Comparison of opioid consumption before and after intrathecal catheter insertion

| Patient | Age (years) | sex | Cause of pain | Equivalent oral morphine before IT (mg/d) * | Equivalent oral morphine after IT (mg/d) * | Maximal inpatient IT infusion rate (ml/h) |
|---|---|---|---|---|---|---|
| 1 | 69 | F | Bed sore | 220 | 30 | 1 |
| 2 | 64 | M | Pelvic metastatic cancer | 375 + methadone 24 mg/d | 60 | 2.5** |
| 3 | 94 | F | Ribs and thoracic vertebra fracture | 200 | 30 | 1 |

* Calculated on the basis of opioid equianalgesic dose conversion table (Montreal University Hospital-CHUM)
**In this patient, the concentration of drugs were modified to avoid passing maximum intrathecal daily dose of bupivacaine
IT Intrathecal;
F female;
M male Case 1: A 69 years old female, with history of laryngeal neoplasia, diabetes and stroke (with hemiparesis) was admitted in hospital for dysphagia and large painful sacral bed sore. Pain was intractable and difficult to control by conventional pain treatment. At the time of admission, she was using gabapentin 2400 mg/day, acetaminophen 3-4 g/day and 25 μg/h fentanyl patch every three days. The fentanyl patch was increased to 50 μg/h and prescribed parenteral morphine as breakthrough dose. A total oral-equivalent morphine daily dose of 220 mg was unsuccessful to control the pain. Due to side effects, it was not possible to increase opioid dose.

Case 2: A 64 years old man with history of end-stage adenocarcinoma of rectum with metastasis to liver and pelvis, sacral plexus involvement due to huge pelvic metastatic mass as 10*14*7 cm was suffering from an excruciating pelvic and sacral pain which was refractory to usual pharmacologic approach (oral or parenteral opioids). Treatment of 30 mg/d parenteral hydromorphone plus 24 mg/d methadone (while resulting in adverse reactions such as hallucination and drug interaction) was unable to control patient's pain.

Case 3: A 94 years old female with multiple thoracic vertebra and ribs fracture (confirmed fracture on T9 without neurological compromise, left 3rd to 6$^{th}$ ribs fracture and suspected fracture on T7, T8, T10 and T11 from imaging analysis) due to falling down, with intractable pain which had made patient bedridden. The pain was difficult to control by conventional pain treatment. Attempt was made to control the pain by prescribing hydromorphone up to 10-15 mg orally or parenterally per day, acetaminophen 4 g/day, celecoxib 200 mg/day, and fentanyl patch up to 50 μg/h every three days. Despite high dose opioid and remarkable side effects, pain was not successfully controlled. Severe pain made the patient unable to exit from complete bedridden situation.

Due to inability to control the pain and remarkable side effects and after discussing with the patients and the attending physicians, it was decided to try IT approach for pain management. An informed consent was obtained from the patients. In all three patients, an IT catheter 20G was placed by percutaneous approach in lumbar area (L2-L3 or L3-L4) advancing to thoracic region and tunneled and fixed subcutaneously. It was connected to an external infusion pump with a mixture of bupivacaine 1 mg/ml, naloxone 0.02 ng/ml, ketamine 100 μg/ml, morphine 0.01 mg/ml and clonidine 0.75 μg/ml. All of them were preservative-free except naloxone which was not available in the market at that time. Starting rate was 1 ml/h. In all of the patients, pain was successfully controlled and oral or parenteral opioid requirements decreased significantly. Acetaminophen was continued as 3-4 g/day in all of them. Infusion rate was adjusted during the following days according to patients' requirement and pain relief (on the basis of visual analog scale in rest time and normal daily activities).

Results: In the first patient, following the catheter insertion and an infusion rate of 1 ml/h, pain decreased dramatically as parenteral morphine was stopped and fentanyl patch was decreased to 12 μg/h. Parenteral hydromorphone was considered as breakthrough during bed sore dressing. Patient analgesic requirement stayed stable with an infusion rate of 1 ml/h or less. The infusion bag was changed every 24 hours. Meanwhile, bed sore healed almost completely. After one month of this regimen, following a fever episode, a sepsis work up was done that showed a urinary and cerebrospinal fluid (CSF) reaction. In spite of immediate parenteral antibiotics, the fever continued. So the catheter was removed. *Klebsiella pneumoniae* was detected in urine and CSF culture. Surprisingly, despite catheter removal, the patient did not request pain medication more than before. She left hospital in good condition without any sequels.

In the second patient, pain was not successfully controlled by parenteral hydromorphone 30 mg/day, methadone 24 mg/day and acetaminophen 3 g/day. Due to opioids and co-analgesics side effects (such as delirium), it was not possible to either increase dosage or to add any other agent. Patient had a history of allergy to morphine. So, a mixture with equivalent dose of preservative-free hydromorphone (a hydromorphine-morphine ratio of 1 to 5) was prepared. Following catheter insertion, pain dramatically decreased with an infusion rate of 1 ml/h. Hydromorphone was used as breakthrough pain control. Due to patient's need, infusion rate was increased to 2.5 ml/h, but to avoid passing the limit of intrathecal bupivacaine daily dose, we changed the mixture as follows: hydromorphone 3 μg/ml, clonidine 1.25 μg/ml, naloxone 2 ng/ml, ketamine 100 μg/ml and bupivacaine 0.7 mg/ml. The infusion bag was changed every 24 hours. At this point, patient occasionally requested hydromorphone. Methadone was decreased and stopped during the following days. Infusion rate was gradually decreased to 1 ml/h and patient left hospital in good condition. For sterility concern, we increased the drugs' concentration during outpatient period. That let us to decrease infusion rate (having the same daily dose) and to change the bag every 72 hours. The catheter was kept in place up to five months out of hospital under the supervision of a family physician. The patient died of his cancer after five months. During the last days of his life, the infusion rate was increased to control the pain and make a comfortable state in terminal phase.

In the third patient, the pain decreased dramatically as hydromorphone no longer had to be used (it was prescribed whenever needed but patient never requested). As supplement, 12 μg/h fentanyl patch every three days and topical lidocaine was used. Infusion rate was gradually decreased to 0.3 ml/hour due to patient pain relief and satisfaction (on the basis of visual analog scale in rest time and normal daily activities) and finally stopped after 2 months. The infusion was stopped at this point and catheter was removed. There was a local irritation in catheter exiting point without any systemic manifestation which was successfully controlled by local care. Patient left hospital in good condition.

There were no remarkable side effects such as catheter's insertion site infection, constipation, muscle weakness, sphincter dysfunction and cognitive or mood deterioration in our patients. Chemical stability testing of the drug mixture was assessed by the Biochemistry Department during a five day period at room temperature. The appearance of the solution was monitored by visual inspection and the drug concentrations were quantified by liquid chromatography coupled to tandem mass spectrometry (LC-MS/MS). No change in appearance was observed during the five day period. The ketamine and bupivacaine concentrations did not change over time. Morphine concentration decreased by approximately 15% on the first day and remained relatively steady during the following days (FIG. 1).

Pain management is a great challenge in elderly and end-stage malignancies. Age-related co-morbidities, polymedication and physiologic changes in elderly limit liberal use of systemic opioids and NSAIDS prescription. In neuroaxial analgesia, IT has less undesirable drug-related side effects due to fewer doses. Moreover, the evidence shows better results for IT approach in comparison with epidural approach in cancer-related pain (2B+ and 2C+ respectively). Morphine, baclofen and ziconotide are the only FDA-approved medications for IT use. Apart from bupivacaine, the others have been used successfully via IT approach at a greater dose than the one we used in our patients (Table-2).

TABLE 2

Comparison of recommended intrathecal daily drugs' doses and our doses

| Product | Recommended dose (9) | Our dose* |
|---|---|---|
| Morphine | 1-20 mg | 0.08-0.24 mg |
| Bupivacaine | 4-30 mg | 8-24 mg |
| Clonidine | 30-1000 μg | 6-18 μg |
| Naloxone | no data available | 0.2-0.5 ng |
| Ketamine | 1-50 mg | 1-2.4 mg |

*Calculated on the basis of ≤1 ml/h infusion rate

In our drugs mixture, morphine, hydromorphone, bupivacaine and clonidine are the drugs that have been already used successfully by IT method (mode). In chronic pain syndromes, morphine is the opioid of first choice for IT administration. It has hydrophilic properties, so, morphine will spread more than fentanyl (and sufentanil) after IT administration and thus extend the area of analgesia. Its presynaptic and postsynaptic effects are via G-protein-linked opioid mu (mainly), delta and kappa receptors. Presynaptic interaction inhibits the release of substance-P and calcitonin gene-related peptide by means of interactions with N-type voltage-dependent calcium channels and reduced calcium influx. Postsynaptic activation of opioid receptors leads to inhibition of adenylate cyclase and also results in opening of potassium channels which, in turn causes hyperpolarization, rendering the postsynaptic second-order neuron less responsive.

Local anesthetics effect is via blocking the Na channels of neuronal tissue and disrupts pain transmission. In the clinical setting, intrathecal bupivacaine dose ranges from 3 to 50 mg/d. The recommended dose of bupivacaine combined with opioids is between 1-14 mg/day and up to more than 30 mg/day did not cause bladder dysfunction or muscle weakness. On the other hand, a dose up to more than 100 mg/day has been reported. In our cases, two patients usually received ≤1 ml/h infusion rate which was equivalent to ≤24 mg/day. The maximum inpatient dose of bupivacaine for the second patient was 42 mg/day.

Clonidine is an alpha2-receptor agonist which is located in both presynaptic and postsynaptic neurons. It reduces presynaptic calcium entry and an increased potassium influx post-synaptically, which initiates hyperpolarization of the postsynaptic cell membrane. Combined with local anesthetics and morphine, it is reported to have a synergistic action for pain relief. IT administration of clonidine (average daily dose range from 50 to 200 µg) reduces the risk of morphine tolerance and thus lessens the risk for opioid-related adverse effects due to dose escalation. Side effects include dry mouth, sedation, bradycardia and hypotension. Sudden discontinuation of long-term IT therapy may lead to rebound hypertension, panic attacks, and psychotic behavior.

Naloxone is an opioid mu-receptor competitive antagonist, but in low dose (in fact "ultra-low dose"), it helps controlling pain and prevents from hyperalgesia. Review of literature suggests that under certain conditions, low-dose opioid antagonists (alone or in combination with opioids) can produce an antinociceptive or analgesic response. Furthermore, they have been used successfully in Crohn's disease and IBS (irritable bowel syndrome) to control disease-associated pain. The possible mechanisms might be upregulation of opioid receptors, increased levels of endogenous opioids, decreased opioid receptor coupling to stimulatory Gs-proteins (mediated through filamin A) and inhibition of opioid agonist-induced activation of glial cells. In a recent study by Mattioli et al., it was demonstrated that co-administration of morphine with ultra-low-dose naltrexone attenuates gliosis in rats, which was noted by an attenuation of increase of the glial proteins GFAP and CD3/CD11B, increase of astrocyte cell volume and astrocyte proliferation. Their IT use alone or in combination with opioids could have analgesic effect, as shown in animal models. In an animal model study, ultra-low dose naloxone enhanced the antihyperalgesia and antiallodynia effects of morphine in rats, possibly by reducing TNF-α and TNFR1 expression and excitatory amino acids (EAAs) such as glutamate and aspartate concentrations in spinal dorsal horn. In a case report, adding 50 ng/day naloxone to IT morphine infusion dramatically enhanced morphine analgesic effect, without apparent side effects for more than 3 years. These mechanisms can explain partly the analgesic effect of our mixture. The mechanistic rationale for naloxone/morphine dose and concentration ratio was on the basis of animal studies and a case report in which an IT naloxone/morphine concentration ratio of $1/10^5$ was efficient to control the pain for three years. One potential concern is remote possibility of naloxone neurotoxicity. It is not approved for IT use but its extremely low concentration, molecular characteristics and animal studies could make it safe for IT use. Molecular structure of naloxone is virtually identical to morphine except in minor moiety substitution at position 9 (or 13). Further, IT naloxone plus morphine in rodents, have not demonstrated signs of spinal cord toxicity. Even, some studies show neural protection of naloxone against ischemic situations. Due to chemical characteristics, ultra-low concentration and animal studies, it seems unlikely that IT naloxone would produce spinal cord toxicity. At the time of our (current) study, naloxone was not available as a formulation without preservative.

Ketamine is an intravenous anesthetic which has analgesic effect in sub-anesthetic doses. Besides, it has antihyperalgesic effect due to the impact on NDMA receptors and anti-allodynic effect by suppressing TLR (toll-like receptor)-mediated signal transduction. It could be used as IT approach in end-stage cancer related pain. Ketamine possesses a plethora of other actions that enhance its analgesic properties. These include blocking non-NMDA glutamate and muscarinic cholinergic receptors, facilitating GABA-A signaling, weakly binding to opioid receptors, and possessing local anesthetics and possibly neuroregenerative properties. It has been used successfully to control cancer and non-cancer pain. But the main concern is possible neurotoxic effect during long-term IT use (even with preservative-free S (+) enantiomer). In one recent animal study, IT injection of a large dose of 1 mg/kg in dogs had no histological alterations of spinal tissue or meninges. Besides, there is more evidence which shows that IT infusion of ketamine would be useful in end-stage cancer related pain. Despite some studies reporting neurotoxicity following IT ketamine, our used dose is much less than the one in these reports and as mentioned previously, the other studies do not show neurotoxic effects in animal models. On the other hand, we should not neglect its beneficial effects in inflammatory process and post-operative outcome. Ketamine is an immunomodulator which prevents the exacerbation and the extension of local inflammation without blunting the local process and delaying inflammatory resolution. This can explain some beneficial aspects of ketamine in post-operative outcome and cognitive dysfunction. Moreover, repeated high dose ketamine might have neurotoxic effect in immature brains in the absence of noxious stimuli whereas it may be neuroprotective in the same brains in the presence of strong painful stimuli. Controversy continues about IT ketamine, but utilizing low-dose preservative-free ketamine in elderly and end-stage malignancies suffering from intractable pain would be a reasonable choice in pain management.

Comparison of systemic opioids consumption (oral and parenteral) before and after catheter insertion shows a significant reduction in daily dose of opioids in our patients (Table-2). The equivalent dose of IT morphine could not explain this reduction. Although there is no consensus about IT to oral opioid conversion rate, compared to maximum conversion ratio calculated by Krames, our doses after catheter insertion are much less than the dose used before. Direct IT infusion, synergistic effect and different mechanisms of action could explain sufficient analgesic effect of our drug combination even at lower concentrations. Due to very low concentration of the drugs (especially ultra-low dose for naloxone), absorption and systemic effect could not be very important in analgesic effect of the mixture.

To achieve a comfortable pain relief in the second patient, we needed larger doses during the short period of admission in hospital and during last days of his life. Severe metabolic changes due to malignancy, progressive tumor invasion, possible tolerance and local aggravated inflammatory processes which interact with prescribed medications' effects could explain a part of this phenomenon.

Physicochemical stability of a drug admixture is assumed if the physical appearance of a solution does not change and drug concentration stays stable. Stability is assumed for an ingredient if the loss is less than 10% of the initial concentration after a period of 96 hours. Our stability assessment shows that bupivacaine and ketamine are sufficiently stable during five days at room temperature (FIG. 1). There is 15%-20% reduction in morphine concentration which may be related to its very low concentration or the other factors. This value is under the critical value for stability but did not decrease further. The infusion bag was changed every 24 hours during hospitalization (inpatient) and every 72 hours at home. No loss of clinical efficacy was observed. It was not possible to effectively assess the stability of naloxone or clonidine at these low concentrations using our LC-MS assay. Meanwhile, their effect on pain reduction is explained by their ultra-low dose concentration. A more precise, accurate and sensitive method for separation and quantification of active ingredients is under development.

Unfortunately, even in IT method for pain management, there are always drug-related complications such as constipation, muscle weakness, sphincter dysfunction and cognitive or mood deterioration. However, we did not observe these side effects as major complications, probably due to positive interaction between the drugs and very low daily dose and concentration.

Achievement of satisfying pain control without major complications by a rate of less than 1 ml/h in our patients could suggest this method as an alternative in elderly patients whose pain could not be well-controlled by conventional opioids. To determine the kind and the dose of probable drugs in mixture, we need more detailed studies with more patients. The main beneficial effect of a drug admixture infusion is to avoid multiple injections. It decreases the risk related to line manipulation, confusion with route of administration, simplify the drug regimen and in some circumstances, facilitates to discharge patient from hospital to care at home. The other advantage of our tested mixture in low concentration and lower daily doses is lower risk of neurotoxicity. But this advantage is not so great compared to the importance of pain control in elderly and end-stage cancer related pain. Having greater number of patients and conducting randomized trials could lead to find more appropriate drug combination.

Pain can be better controlled by multi-drug intrathecal infusion for a short time in advanced-age and end-stage malignancies. The advantages of this method are the better pain control and less systemic side effects due to lower prescribed doses.

EXAMPLE 2

Pain Management Through Infusion in the Right Brachial Plexus

A 66 year old patient having suffered a subarachnoid hemorrhage (SAH grade II) following a ruptured aneurysm of the carotid, suffered from a middle cerebral left vasospasm. The patient exhibits a severe spastic right hemiparesis post stroke. Spasticity results in significant pain due to contractures and poor positioning of the right arm. It has dysesthesia, allodynia and hyperalgesia to the touch surface. The patient also presents a problem of aphasia, but nevertheless communicates very well.

Conventional treatments for pain and medication trials (Botox in 2011, Baclofen 10 mg bid in 2013) have yielded very little results and provide no relief.

The patient is seen in the pain clinic since February 2014 where intravenous infusions of ketamine were well tolerated, but did not provide any relief to the level of pain. Since November 2015, blocks were made to brachial plexus level of the right arm with an analgesic solution with very little success.

In January 2016, the patient was installed with a catheter with a port-a-carth at the right brachial plexus. The patient is treated with a formulation according to the present invention comprising bupicaine, morphine, naloxone, ketamine, and clonidine. The patient has received 6 treatments so far, all of which have been injected via the catheter port-a-cath. In the space of seven weeks of treatment (between Feb. 18 and Apr. 13, 2016), the patient saw a vast improvement in pain: the pain scale decreased from a 7-9 on a scale of 10, to a 0-2 on a scale of 10.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:
1. A formulation useful for pain control comprising:
   morphine at a daily dose of between 0.08 to 0.24 mg;
   bupivacaine at a daily dose of between 8 to 24 mg;
   clonidine at a daily dose of between 6 to 18 µg;
   naloxone at a daily dose of between 0.2 to 0.5 ng; and
   ketamine at a daily dose of between 1 to 2.4 mg.
2. The formulation of claim 1, useful for administration intrathecally, epidurally, paravertebrally, at the peripheral nerves level, at the nerve plexus level, intraarticularly, in a synovial bursa, sub-cutaneously, and intravenously, or combination thereof.
3. A method of pain control which comprises administration to a patient in need thereof the formulation of claim 1.
4. The method of claim 3, wherein administration is intrathecal, epidural, paravertebral, at the peripheral nerves level, at the nerve plexus level, intraarticular, in a synovial bursa, sub-cutaneous, or intravenous, or combination thereof.

* * * * *